US010485497B2

(12) United States Patent
Speeg et al.

(10) Patent No.: US 10,485,497 B2
(45) Date of Patent: Nov. 26, 2019

(54) SURGICAL PROBE APPARATUS AND SYSTEM AND METHOD OF USE THEREOF

(71) Applicant: Devicor Medical Products, Inc., Cincinnati, OH (US)

(72) Inventors: Trevor W. V. Speeg, Williamsburg, OH (US); Michael E. Henley, Liberty Township, OH (US); Brian Michael Ruffner, Maineville, OH (US); Michael B. Watts, Beavercreek, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 15/963,152

(22) Filed: Apr. 26, 2018

(65) Prior Publication Data

US 2018/0235556 A1    Aug. 23, 2018

Related U.S. Application Data

(63) Continuation of application No. PCT/US2016/058907, filed on Oct. 26, 2016.
(Continued)

(51) Int. Cl.
*G06T 1/20* (2006.01)
*A61B 6/00* (2006.01)
(Continued)

(52) U.S. Cl.
CPC .............. *A61B 6/4057* (2013.01); *A61B 6/12* (2013.01); *A61B 6/425* (2013.01); *A61B 6/4258* (2013.01);
(Continued)

(58) Field of Classification Search
CPC ......... G01T 1/169; G01T 1/161; G01T 1/202; G01T 1/244; G01T 1/2023; A61B 6/4057;
(Continued)

(56) References Cited

U.S. PATENT DOCUMENTS 4,782,840 A    11/1988   Martin et al.
4,889,991 A    12/1989   Ramsey et al.
(Continued)

OTHER PUBLICATIONS

International Preliminary Report on Patentability dated May 1, 2018 for Application No. PCT/2016/058907, 7 pgs.
(Continued)

*Primary Examiner* — Kiho Kim
(74) *Attorney, Agent, or Firm* — Frost Brown Todd LLC

(57) ABSTRACT

In the field of radioimmunoguided surgical system instrumentation there is described and claimed a hand-held probe with a disposable power source as well as a visually perceptible indicator of detected counts of radiation. Also disclosed is a system comprising the hand-held probe and an instrumentation console. The handle includes a probe link that transmits a message containing gamma data relating to the low-level electrical signal. The instrumentation console may include a housing, a console link to receive the message transmitted by the probe link, a receiver electrically coupled to the console link to convert the message to corresponding electrical display signals, and a visually perceivable display electrically coupled to the receiver to convert the electrical display signals to a visually perceivable display relating to the amount of radiation detected.

13 Claims, 10 Drawing Sheets

Related U.S. Application Data

(60) Provisional application No. 62/247,082, filed on Oct. 27, 2015.

(51) Int. Cl.
*G01T 1/161* (2006.01)
*G01T 1/202* (2006.01)
*A61B 6/12* (2006.01)
*G01T 1/24* (2006.01)
*A61B 17/00* (2006.01)

(52) U.S. Cl.
CPC .......... *A61B 6/4405* (2013.01); *A61B 6/4423* (2013.01); *G01T 1/161* (2013.01); *G01T 1/202* (2013.01); *G01T 1/244* (2013.01); *A61B 2017/00079* (2013.01); *G01T 1/2023* (2013.01)

(58) Field of Classification Search
CPC ......... A61B 6/12; A61B 6/425; A61B 6/4258; A61B 6/4405; A61B 6/4423; A61B 2017/00079
See application file for complete search history.

(56) References Cited

U.S. PATENT DOCUMENTS

| | | | |
|---|---|---|---|
| 5,441,050 A | 8/1995 | Thurston et al. | |
| 5,495,111 A | 2/1996 | Thurston et al. | |
| 5,732,704 A | 3/1998 | Thurston et al. | |
| 5,916,167 A | 6/1999 | Kramer et al. | |
| 5,961,458 A * | 10/1999 | Carroll | A61B 6/032 250/336.1 |
| 6,123,454 A * | 9/2000 | Canfield | G01J 5/021 374/158 |
| 6,144,876 A | 11/2000 | Bouton | |
| 6,191,422 B1 | 2/2001 | Thurston | |
| 6,204,505 B1 | 3/2001 | Call | |
| 6,218,669 B1 | 4/2001 | Call | |
| 6,222,193 B1 | 4/2001 | Thurston et al. | |
| 6,259,095 B1 | 7/2001 | Bouton et al. | |
| 6,272,373 B1 | 8/2001 | Bouton | |
| 7,476,859 B2 | 1/2009 | Tomita et al. | |
| 8,227,766 B2 | 7/2012 | Chapman | |
| 8,269,185 B2 | 9/2012 | Call | |
| 9,671,504 B2 | 6/2017 | McFerron | |
| 2005/0230628 A1* | 10/2005 | Hirai | G01T 1/169 250/370.01 |
| 2006/0266948 A1* | 11/2006 | Hofstetter | G01T 1/161 250/370.01 |
| 2006/0276738 A1* | 12/2006 | Becker | A61F 9/00772 604/8 |

OTHER PUBLICATIONS

European Examination Report dated May 29, 2019 for Application No. EP 16794138.4. 6 pgs.

* cited by examiner

SURGICAL PROBE APPARATUS AND SYSTEM AND METHOD OF USE THEREOF

RELATED APPLICATION

The present Application for Patent claims priority to U.S. Provisional Application No. 62/247,082 entitled "SURGICAL PROBE APPARATUS AND SYSTEM AND METHOD OF USE THEREOF" filed Oct. 27, 2015, which is assigned to the assignee hereof, and incorporated herein by reference in its entirety.

FIELD OF THE INVENTION

The present invention relates generally to radioimmunoguided surgical system instrumentation, in particular to a probe for use with such a system.

BACKGROUND OF THE INVENTION

Procedures for the treatment of cancer generally have been based upon the natural history of tumor spread, and thence, upon operative and non-operative options available to the physician. Operative options generally have looked to the physical identification and surgical resection of tumor(s). A variety of techniques have been brought to bear in the art with the purpose of aiding the surgeon in detecting and localizing neoplastic tissue as part of this surgical procedure. ("Neoplastic tissue," for the present purposes, often is referred to as cancerous tissue, though malignant tumor and malignant tumor cells also are found in the terminology of the art. The term "neoplastic tissue" includes all of these.) Typically, large tumor(s) are readily located by the surgeon by visualization at the operating theater, and, in particular, through palpation, i.e., the feel of a tumor as opposed to that of normal tissue. To achieve operative success, however, it is necessary for the surgeon to somehow locate "occult" tumor(s), i.e., tumor(s) that cannot be located by the conventional surgical procedures of sight and feel. Failure to locate and remove such occult tumor(s) generally will result in the continued growth of cancer in the patient, a condition often referred to as "recurrent" cancer.

A much improved method for locating, differentiating, and removing neoplasms uses a radiolabeled antibody injected into the patient. Once injected, such antibodies are known to accumulate in neoplastic tissues at a higher concentration than in normal tissue. A portable radiation detection probe is employed by a surgeon intraoperatively in order to detect sites of radioactivity. Because of the proximity of the detection probe to the labeled antibody, the faint radiation emanating from occult sites becomes detectable, for example, in part because of the inherent application of the approximate inverse square law of radiation propagation. The procedure is known as radioimmunoguided surgery.

It is generally also thought that the spread of certain types of solid tumor cancers is caused by the migration (or draining) of tumor cells from the initial tumor to nearby lymph nodes and eventually to other vital sites via the lymphatic system. Cancer surgeons and medical oncologists believe the determination of whether a patient's primary tumor has spread to the lymph nodes is a major determinant of a patient's long-term prognosis. The spread of cancer to the patient's lymph nodes is established by the examination of the nodes by pathology to determine if tumor cells are present. If tumor cells are determined to be present in the lymph nodes, the patient's stage or severity of disease is increased. Surgeons perform procedures to identify the draining node(s) through the injection of a radioactive tracing agent at the site of the primary tumor. Following injection, the tracing agent follows the drainage path of the tumor to the nearest lymph node or nodes, referred to as the "sentinel node(s)." A gamma detection device is used to detect the path of the tracing agent. Since the lymph nodes are connected, oncologists believe that if the sentinel nodes show no sign of malignancy, then the downstream nodes in the pathway are likely to be clear of disease. As such, the removal of other nearby lymph nodes would be clinically unnecessary. Therefore, the ability to rapidly locate and biopsy sentinel nodes provides vital information to the physician in determining if the cancer has spread or if it is localized to the site of the primary tumor.

Recent technologies now allow the surgeon, via a combination of both isotopically labeled drugs and hand-held radiation detection devices, to provide enhanced surgical evaluation of tumor dissemination, e.g., removal of primary tumor-associated lymph nodes. Such surgical radiation detection instrumentation is comprised generally of a handheld probe that is in electrical communication with a control console via a flexible cable or, more recently, via wireless communication. This control console is located within the operating room facility but out of the sterile field, while the hand-held probe and forward portions of its associated cable are located within that field. The hand-held radiation detecting probe is relatively small and performs in conjunction with a semiconductor detector such as cadmium zinc tellurium or a scintillating material such as or cesium iodide. Example instrumentation may be found in U.S. Pat. No. 4,782,840 and U.S. Pat. App. Pub. No. 2009/0326371, the disclosure of each of which is expressly incorporated by reference in its entirety herein.

A commercially available system and equipment to perform this radiation detection during surgery is the "Neoprobe Gamma Detection System", available from Devicor Medical Products, Inc. Cincinnati, Ohio. See http://www-.mammotome.com/neoprobe/.

Radioactive sources have been detected directly at whatever energy levels the source of radiation is producing by using detectors comprised of semiconductor (e.g., cadmiumzinc-tellurium) or scintillating (e.g., cesium iodide) materials. An output signal is produced when an incoming photon collides with material within the detector. The higher the energy level of the primary source of radiation, the more incoming photons can pass completely through the detector without colliding with any material, thus producing no output from the detector. For this reason, high energy detectors have necessarily been made of relatively "thick" (i.e., large cross-section volume) and dense materials to assure that a sufficient number of collisions occur to provide usable detector sensitivity. This characteristic of the detector is often referred to as "stopping power" or "absorption efficiency."

In order to more efficiently detect high-energy radiation, it is usually necessary to increase the detector absorption by increasing the thickness of the detector crystal. Alternatively, a stacked crystal array having the absorption efficiency of a relatively thick monolithic crystal that may be biased with a relatively low voltage may be used. A stacked crystal array is described in U.S. Issued U.S. Pat. No. 8,269,185, "STACKED CRYSTAL ARRAY FOR DETECTION OF PHOTON EMISSIONS", issued 18 Sep. 2012, which is hereby expressly incorporated by reference in its entirety herein.

U.S. Pat. No. 6,144,876, "SCANNING A RADIATION SOURCE WITH A COUNT RATE OUTPUT DERIVED

WITH A DYNAMIC WINDOW ANALYSIS", issued 7 Nov. 2000. This patent describes and claims a system in which count rate outputs of a probe-based radiation detection system are stabilized through the utilization of a dynamic window-based count analysis. Circular memory is utilized to record a sequence of segment count values. These values then are accessed and updated with respect to short scan intervals. The memory segments then are employed to develop a count sum over a count collection interval. That count sum is employed with algorithms adjusting the upper and lower edges of the dynamic window. A reported mean value, computed from the window upper edge or window lower edge, is utilized for creating a variable pitch output or for driving a bar graph. Background count and target count intervals are adjusted utilizing a data point predictive technique in combination with upper and lower time bounds.

U.S. Pat. No. 6,191,422, "RADIATION PROBE WITH COMPOUND SEMICONDUCTOR CRYSTAL PERFORMING IN A TRAPPING-DEPENDENT OPERATIONAL MODE" issued on 20 Feb. 2001. This patent describes and claims a hand-held radiation probe {which is configured} having a crystal thickness as well as a bias generated electrical field which have values to cause the semiconductor crystal to operate in a trapping-dependent operational mode wherein a trapping of substantially all carriers generated by radiation impinging upon the crystal forward face are trapped. The bias level voltage is selected to achieve adequate photopeak heights and to permit the windowing out of lower energy Compton scattering and other noise phenomena.

U.S. Pat. No. 6,218,669, "SURGICAL PROBE APPARATUS", issued on 17 Apr. 2001. This patent describes and claims a surgical probe apparatus which incorporates a probe structure with a handle component and forward crystal mount wherein a cadmium-telluride crystal is rigidly mounted against movement. A cup-shaped window assembly is provided having an internal cylindrical tungsten shield which extends forwardly from the front face of the crystal to define an air gap as well as to support an aluminum window. The window assembly is threadably mounted upon the handle at a transition region forming an outwardly extending ramp. This ramp is used in conjunction with a polymeric retainer component with legs containing dog structures which hold a cylindrical tungsten collimator in biased position against the window when attached.

U.S. Pat. No. 6,259,095, "SYSTEM AND APPARATUS FOR DETECTING AND LOCATING SOURCES OF RADIATION" issued on 10 Jul. 2001. This patent describes and claims a system and apparatus for locating sources of radiation emanating from predetermined radionuclides. The apparatus incorporates a large window display utilizing icon imagery to identify counting functions such as target count and background. A variety of radionuclide modes of operation can be selected by the operator and the system automatically defaults to detector bias selection and window reference voltage selection in correspondence with the elected radionuclide. A bar graph readout apprises the user of the amount of time or count level remaining in a target or background procedure and the flashing of icon identifiers occurs during such procedures. Pulse validation is improved by the utilization of a discriminator which evaluates pulse width.

U.S. Pat. No. 6,272,373, "SCANNING SYSTEM AND METHOD FOR LOCATING SOURCES OF RADIATION EMISSION", issued 7 Aug. 2001. This patent describes and claims a scanning system for a hand-held probe employing a 50 ms scanning interval in conjunction with circular memory. Combinations of segment bins from the circular memory are acquired following each short scanning interval. A threshold is computed for each combination initially based upon a threshold factor which is statistically significant and has a value of three. Audible cueing is developed if any three of six of these combinations of segment bin scan counts exceeds a correspondingly computed threshold value. Thereafter, the threshold factor is diminished to a value of one and the same thresholding tests are carried out to maintain audible cueing. Running count rates are computed as the average of the entire circular buffer memory divided by its corresponding total collection time. This computation is provided on a one half second updated basis.

All of the above issued US Patents are expressly incorporated by reference in their entirety herein.

The above-described systems can be burdensome because the entire probe unit (including detector and handle), must be sterilized between every use. Furthermore, the entire probe unit must be replaced or sent for repair if a malfunction occurs in any part. Thus, there is a need in the art for a probe that avoids these problems.

SUMMARY OF THE INVENTION

The first aspect of the instant claimed invention is a hand-held probe including:
  a detector having a first mating component and being configured to generate a low-level electrical signal relating to a radiation source proximate the detector; and
  a handle comprising a second mating component configured to removably mate with the first mating component such that the handle is removably coupleable with the detector.

The second aspect of the instant claimed invention is a system, comprising:
  a hand-held probe including: a detector having a first mating component and being configured to generate a low-level electrical signal relating to a radiation source proximate the detector; and a handle comprising: a second mating component configured to removably mate with the first mating component such that the handle is removably connectable with the detector;
a probe link configured to transmit a message containing gamma data relating to the low-level electrical signal; and an instrumentation console including: a housing; a console link within the housing and configured to receive the message transmitted by the probe link; a receiver electrically coupled to the console link to convert the message to corresponding electrical display signals, and a visually perceivable display electrically coupled to the receiver to convert the electrical display signals to a visually perceivable display relating to the amount of radiation detected.

The third aspect of the instant claimed invention is a method of conducting radioimmunoguided surgery comprising:
  providing a detector having a first mating component and being configured to generate a low-level electrical signal relating to a radiation source proximate the detector; providing a handle comprising a second mating component configured to removably mate with the first mating component such that the handle is removably connectable with the detector; and coupling the detector with the handle by mating the first mating component with the second mating component.

Additional advantages and novel features of various aspects of the present invention will be set forth in part in the description that follows, and in part will become more apparent to those skilled in the art upon examination of the following or upon learning by practice thereof.

DETAILED DESCRIPTION

Figure 1:
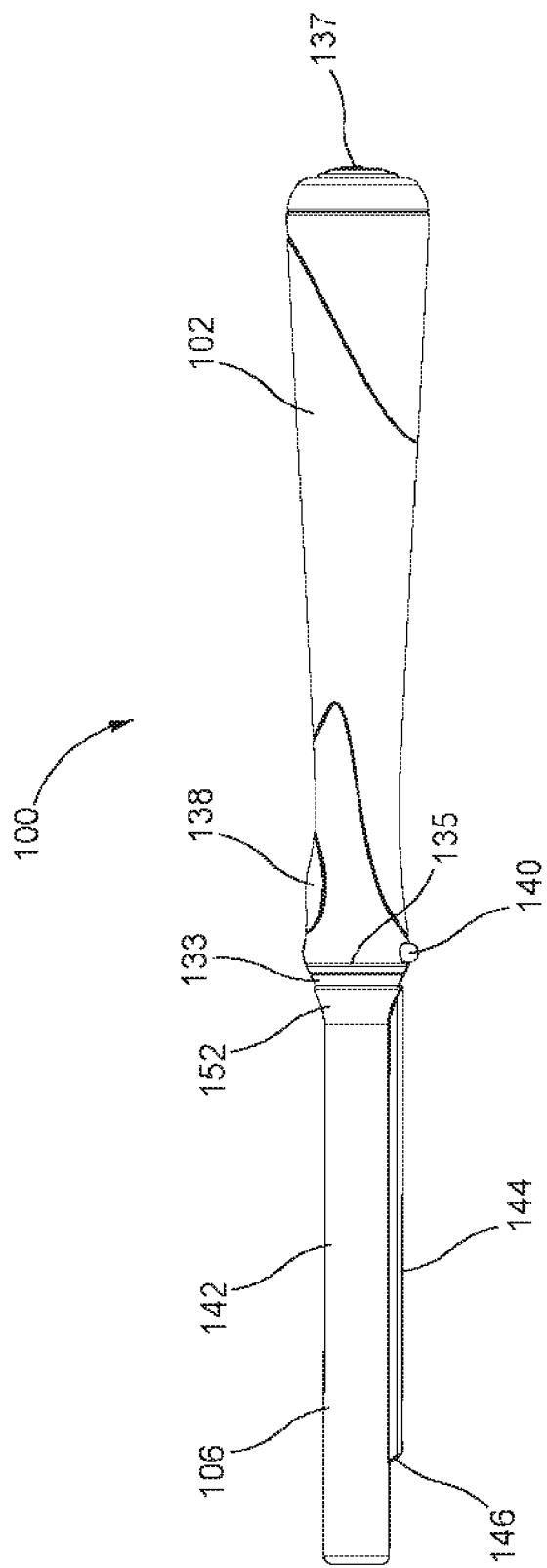
FIG. 1 is a side view of an example probe in accordance with aspects of the present invention.

The following description of certain examples of the invention should not be used to limit the scope of the present invention. Other examples, features, aspects, embodiments, advantages, and one of the best modes contemplated for carrying out of the invention will become apparent to those skilled in the art from the following description, which is by way of illustration only, and in no way designed to limit the scope of the present invention. As will be realized, the present invention is capable of other different and obvious aspects, all without departing from the scope of the present invention. Accordingly, the drawings and descriptions should be regarded as illustrative in nature and not restrictive.

In an aspect of the present invention a hand-held probe comprises a detector having a first mating component and being configured to generate a low-level electrical signal relating to a radiation source proximate the detector; and a handle comprising a second mating component configured to removably mate with the first mating component such that the handle is removably coupleable with the detector.

Other aspects may include a system, comprising a hand-held probe and an instrumentation console. The hand-held probe may include a detector having a first mating component and being configured to generate a low-level electrical signal relating to a radiation source proximate the detector and a handle. The handle may comprise a second mating component configured to removably mate with the first mating component such that the handle may be removably connectable with the detector; and a probe link configured to transmit a message containing gamma data relating to the low-level electrical signal. The instrumentation console may include a housing, a console link within the housing configured to receive the message transmitted by the probe link, a receiver electrically coupled to the console link to convert the message to corresponding electrical display signals, and a visually perceivable display electrically coupled to the receiver to convert the electrical display signals to visually perceivable signals relating to the amount of radiation detected.

Other aspects include a method comprising providing a detector having a first mating component and being configured to generate a low-level electrical signal relating to a radiation source proximate the detector, providing a handle comprising a second mating component configured to removably mate with the first mating component such that the handle is removably connectable with the detector, and coupling the detector with the handle by mating the first mating component with the second mating component.

| Parts List | |
|---|---|
| Part Names | Number |
| probe | 100 |
| handle | 102 |
| detector | 104 |
| sheath | 106 |
| first mating component | 108 |
| end | 110 |
| free end | 112 |
| projection | 114 |
| electrical contact | 115 |
| slots | 116 |
| protrusions | 118 |
| body | 120 |
| body | 122 |
| free end | 124 |
| opposing end | 126 |
| second mating component | 128 |
| projection | 130 |
| slot | 132 |
| flange | 133 |
| protuberances | 134 |
| light ring | 135 |
| light emitter | 136 |
| power switch | 137 |
| switch | 138 |
| pivot point | 140 |
| body | 142 |
| channel | 144 |
| end | 146 |
| open first end | 148 |
| open second end | 150 |
| lip | 152 |
| probe | 200 |
| detector | 204 |
| opposing end | 210 |
| free end | 212 |
| elongated body | 220 |
| longer light emitter | 236 |
| probe | 300 |
| detector | 304 |
| opposing end | 310 |
| free end | 312 |
| elongated body | 320 |
| probe | 400 |
| handle | 402 |
| detector | 404 |
| sheath | 406 |
| first mating component | 408 |
| opposing end | 410 |
| free end | 412 |
| flange | 414 |
| ribs | 416 |
| electrical connection component | 418 |
| elongated body | 420 |
| body | 422 |
| free end | 424 |
| opposing end | 426 |
| second mating component | 428 |
| light emitter | 436 |

-continued

Parts List

| Part Names | Number |
| --- | --- |
| power/wireless pairing button | 437 |
| light button | 438 |
| body | 442 |
| sleeve | 444 |
| open first end | 448 |
| opposing open second end | 450 |
| lip | 452 |
| console | 500 |
| graphical user interface | 501 |
| probe indicator | 502 |
| selectable dynamic pitch range indicator | 504 |
| numerical measure count | 506 |
| numerical target count | 508 |
| graphical representation | 510 |
| user selectable volume range | 512 |
| computer system | 900 |
| display interface | 902 |
| processor | 904 |
| communication infrastructure | 906 |
| main memory | 908 |
| secondary memory | 910 |
| hard disk drive | 912 |
| removable storage drive | 914 |
| removable storage unit | 918 |
| communications interface | 920 |
| removable storage unit | 922 |
| communications interface | 924 |
| path | 926 |
| signals | 928 |
| display unit | 930 |
| hard disk drive | 970 |
| removable storage drive | 980 |
| communication system | 1000 |
| terminals | 1042 |
| server | 1043 |
| network | 1044 |
| couplings | 1045 |
| couplings | 1046 |
| accessors | 1060 |
| accessors | 1062 |
| couplings | 1064 |
| terminals | 1066 |

Figure 2:
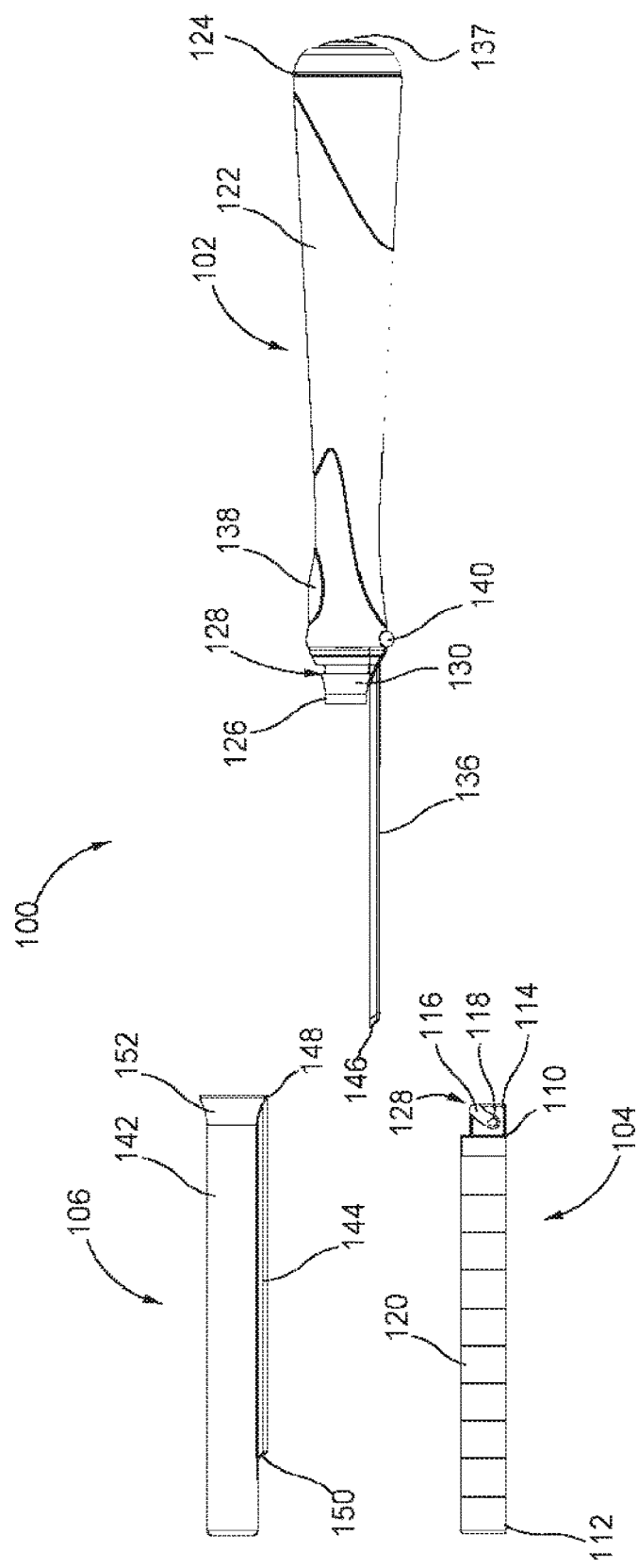
FIG. 2 is an exploded side view of the probe of FIG. 1.
Figure 3:
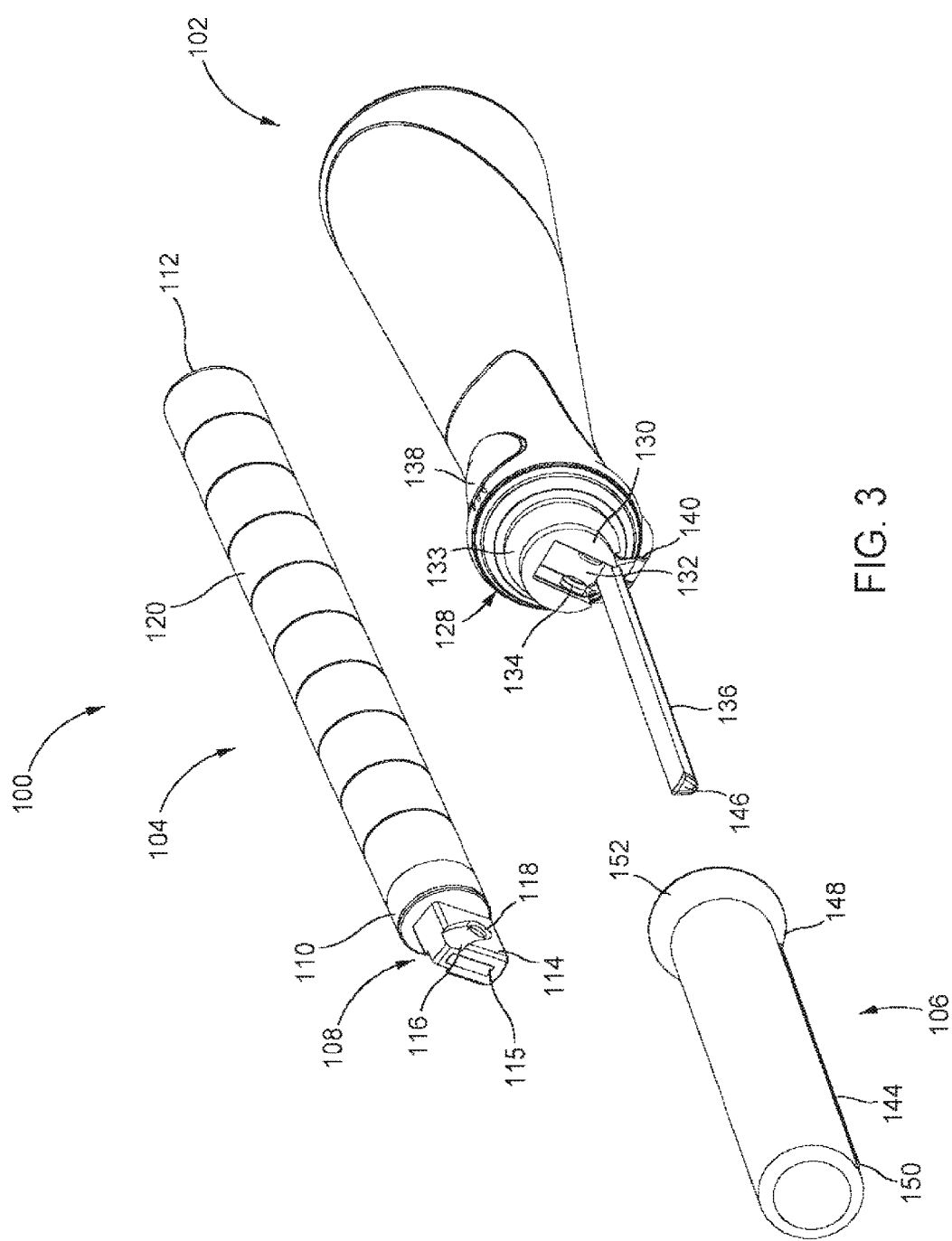
FIG. 3 is an exploded perspective view of the probe of FIG. 1.

FIG. 1 shows a side view of an example probe 100 in accordance with aspects of the present invention. FIG. 2 shows an exploded side view of the probe 100. FIG. 3 shows an exploded perspective view of the probe 100. As shown in FIGS. 1 and 2, the probe 100 may generally include a handle 102, a detector 104, and in some aspects, a sheath 106.

The detector 104 may be configured to generate a low-level electrical signal relating to a radiation source proximate to the detector, e.g., the detector may be a radiation detector. The detector 104 may comprise cadmium zinc telluride or any other semiconductor material suitable for detecting photon radiation. More broadly, detector 104 may include any suitable type of crystal that is responsive to gamma radiation emitted by radiolabeled antibodies. For example, detector 104 may comprise cadmium-telluride crystals with or without an alloy, for example, an alloy with zinc. Such alloys for the present description may generally and interchangeably be referred to as "Cadmium-telluride" or "CdTe" and "Cadmium zinc telluride" or "CZT." Details of exemplary CZT crystals may be found in U.S. Pat. Nos. 5,441,050, 5,495,111, 6,191,422 and 6,218,669 the entire contents of which are hereby expressly incorporated by reference herein. Another example CZT crystal can be found in U.S. Pat. No. 8,269,185, "STACKED CRYSTAL ARRAY FOR DETECTION OF PHOTON EMISSIONS", issued 18 Sep. 2012. The entire contents of U.S. Pat. No. 8,269,185 are hereby expressly incorporated herein, referring in particular to the discussion of the plurality of crystal slices, the pair of crystal interconnects, the pair of insulators, and the housing. Alternatively, the detector 104 may be a scintillating device. The scintillating device may be any type of particle or radiation detector, now known or later developed, for detecting and counting scintillations produced by ionizing radiation, including but not limited to, cesium iodide. For example, the detector 104, configured as a scintillating device, may operate through emission of light flashes that are detected by a photosensitive device, such as a photomultiplier or a silicon PIN diode.

The detector 104 may generally include an elongated body 120 having a free end 112 and an opposing end 110 for connecting to the handle 102. The crystal slices and other components as described in U.S. Pat. No. 8,269,185 would be located within the body 120 at the free end 112 of the detector 104. The detector 104 may include a first mating component 108, which is best seen in FIGS. 2 and 3. The first mating component 108 may be configured to mate with a second mating component 128 of the handle 102, discussed below. The first mating component 108 may be located at the end 110 of the detector opposite the free end 112. The first mating component 108 may be configured to have a structure that mates with the mating component 128 of the handle 102 and may provide both structural support and an electrical connection. For example, the first mating component 108 may include a projection 114 having a slots 116 terminating in protrusions 118. As seen by comparing FIG. 2 and FIG. 3, a slot 116 and a protrusion 118 may be located on each side of the projection 114. The projection 114, slot 116, and projections 118 together may mate with corresponding features of the handle to provide physical support and an electrical connection. The first mating component 108 may further include an electrical contact 115 on an end face of the projection 114.

The handle 102 may be sized and shaped for gripping by a human hand, e.g., a medical practitioner. Thus, the probe 100 may be hand-held. The handle 102 may generally comprise a body 122 having a free end 124 and an opposing end 126 for connecting to the detector 104. The handle 102 may generally include the electrical and computer components of the system to provide power to the detector 104 and communicate with an instrumentation console. For example, the handle 102 may include within a single body 122, a power source (e.g., a disposable or rechargeable battery, preferably disposable), a preamplifier, a controller, a probe data link, and photo-electronics. Preferably, the probe data link may be a wireless data link. Each of these components is described in U.S. Pat. App. Pub. No. 2009/0326371, which is hereby expressly incorporated by reference herein.

The amplifier receives and amplifies the low-level electrical signal generated by detector 104 to a corresponding output electrical signal of greater magnitude (i.e., voltage and current). The preamplifier may also supply an electrical bias voltage to detector 104 to effect charge migration in the detector 104 when it is exposed to gamma radiation. Details of example preamplifiers may be found in U.S. Pat. Nos. 6,204,505 and 6,222,193 each of which is hereby expressly incorporated by reference herein. The controller may receive the output electrical signal from the preamplifier and may analyze the output electrical signal to derive gamma data corresponding to the amount of gamma energy detected by the detector 104. In some embodiments, the gamma data may be in the form of "counts," relating to the number of detected photon radiation impingements. Further details may be found in U.S. Pat. No. 4,889,991, hereby expressly incorporated by reference herein. The controller may also be configured with a control switch to allow a user of the probe to set predetermined operating parameters of the probe including, without limitation, a real-time radiation target count and a time-interval accumulated count, and calibration/test. Parameters may be selected by actuating a control switch for a predetermined period of time, or by actuating the control switch a predetermined number of times within a predetermined period of time.

The controller may be a digital microprocessor-based control unit configured to operate according to a predetermined control logic to provide control signals for controlling the operation of the probe. Alternatively, the controller may comprise other types of digital-based architectures utilizing, for example, a computer, microcontroller, programmable logic device and the like. The control logic of the controller may be defined by a set of predetermined instructions, such as a computer program or "fuzzy logic." The controller may also comprise analog circuitry in whole or in part.

The probe data link may be configured for operation in conjunction with an associated instrumentation console data link of a console to transfer data between the probe and the console. The probe link may be implemented in any form now known or later invented utilizing, without limitation, radio frequency (RF), visible light, infra-red light, sonic and ultrasonic links and any conventional type of analog or digital modulation including, without limitation, amplitude modulation, frequency modulation, phase shift keying and frequency shift keying. Telecommunication protocols such as the BLUETOOTH® standard as promulgated by the Bluetooth Special Interest Group, Inc. (SIG) may also be employed. An example aspect may employ a protocol, such as BLUETOOTH®. Alternatively, a proprietary communication protocol may be utilized.

The handle 102 may include a second mating component 128 for mating with the first mating component 108 of the detector 104. The second mating component 128 may include mating features that correspond with the mating of the first mating component 108, which allow for the detector 104 to be removably connected with the handle 102. For example, the second mating component 128 may include a projection 130 having a slot 132 and a pair of protuberances 134 protruding from the sidewalls that define the slot 132. As best seen in FIG. 3, the projection 114 of the first mating component 108 may be sized and shaped to fit within the slot 132 of the second mating component 128. Furthermore, the opposing slots 116 of the first mating component 108 may be sized and shaped to receive the pair of protuberances 134 of the second mating component 128. The slots 116 may serve the function of guiding the protuberances 134 as the mating components are mated. The protuberances 118 of the first mating component 108 may be further sized to contact and/or mate with the protuberances 134 of the second mating component 128. For example, one of or both of protuberances 118, 134 may be spring loaded in a direction toward each other so that the protuberances 118, 134 remain in contact during operation. In another aspect, a mechanical feature may be used to maintain contact such as a detent mechanically releasable through a trigger. Upon fully mating the first and second mating components together, the electrical contact 115 of the detector 104 is in contact with a corresponding electrical contact in the handle 102 thereby providing power and communication with the above-described controller/computer components in the handle. The handle 102 can be unmated with the detector 104 by pulling the detector away from the handle 102 and reversing the mating steps.

Figure 4:
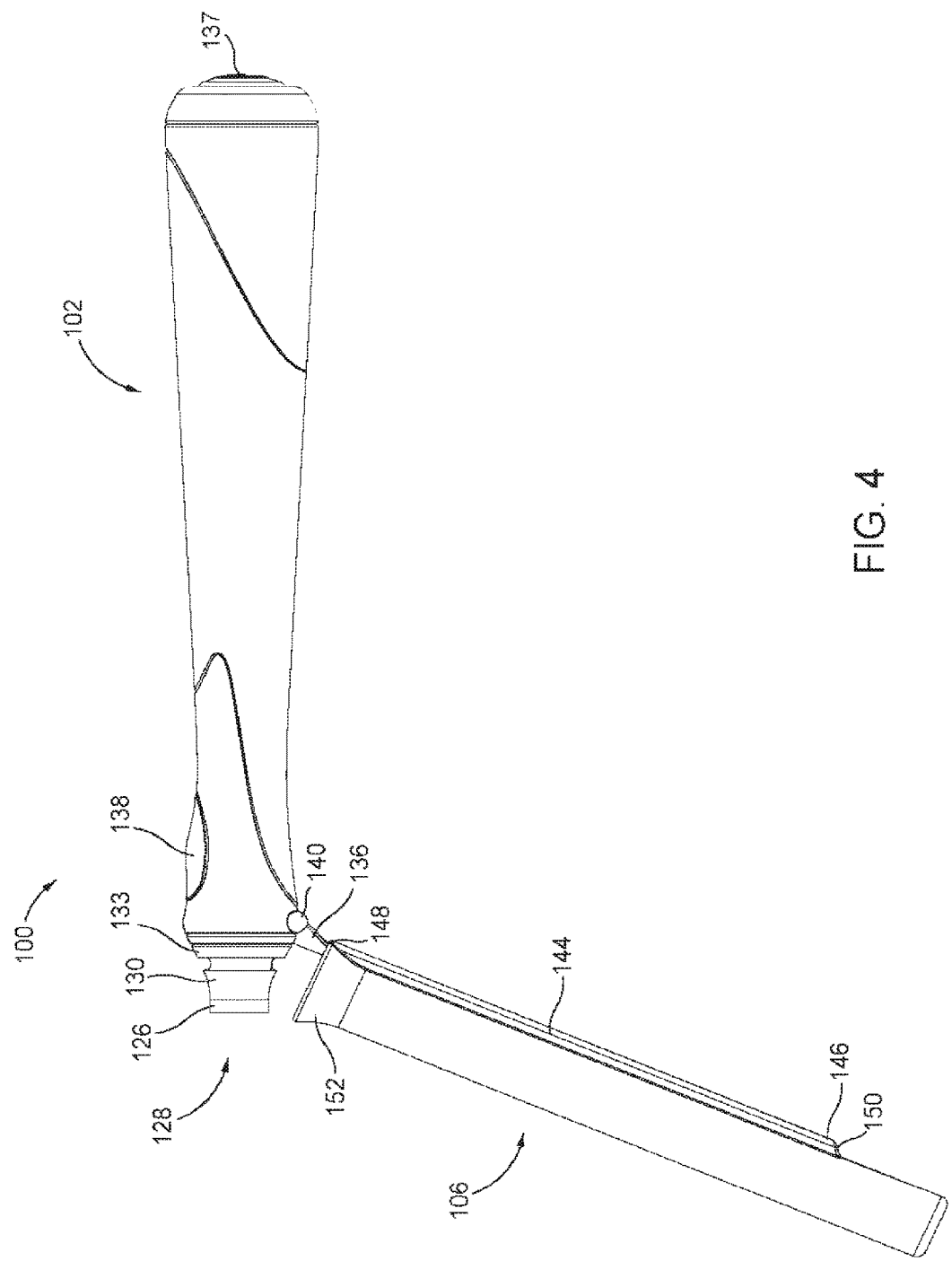
FIG. 4 is a side view of the probe of FIG. 1 in a pivoted orientation.

The handle 102 may further include a light emitter 136. The light emitter may be a single-bound fiber optic cable, for example being made of a clear plastic such as acrylic plastic. The light may propagate along and be emitted along the entire length and/or at the opposing end 146 of the fiber optic cable. In another aspect, the light emitter 136 may be a light emitting diode (LED) at the end 146, with wires extending back into the handle. In yet another aspect, the light may originate from a light source in the handle, and the light emitter 136 may be a light piping material that contains and directs the light through and out the other end of the piping. The handle 102 may include the photo-electronics used for providing power and controlling the light emitted by the fiber optic cable/LED. For example, the handle 102 may further include a switch 138 for controlling when light is emitted by light emitter 136. The switch 138 may be an on/off toggle switch where each press of the switch 138 turns the light on or off until pressed again or it may be a deadman type switch where the light remains off unless the switch 136 is held down by the operator. The light emitter 136 may be pivotally coupled to the handle 102 via a pivot point 140. FIG. 4 shows the light emitter 136 in a pivoted position, which is discussed in more detail below. The handle 102 may further include a light ring 135. The light ring 135 may be configured to light up in conjunction with operation of the detector when detecting radiation. The light ring 135 may provide visual feedback to the operator regarding the measured counts, which is discussed below in more detail with respect to operating the probe. The handle 102 may further include a power switch 137 for turning on the probe 100 and/or for pairing the probe 100 with the instrumentation consoles via a wireless connection. The handle may further include flange 133. The function of flange 133 is described below.

The probe 100 may further include a sheath 106. The sheath 106 may generally comprise an elongated hollow body 142 that is be shaped and sized to fit around the detector 104. The sheath may comprise a relatively inexpensive sterilizable material, for example, silicone plastic. Prior to distribution to the operator, the sheath may be pre-sterilized using any suitable sterilizing technique, for example, ethylene oxide ("ETO") sterilization. A plurality of pre-sterilized sheaths may be delivered to the operator so that the operator may dispose of the sheath after one-time use, which is explained below with respect to the operating method. Because the sheaths are pre-sterilized, the operator does not necessarily need to sterilize the detector 104 after each use and can simply throw away and use a new sheath for each detection. The sheath 106 may have a shape substantially corresponding to and/or congruent with the shape of the detector 104. The inside surface of the sheath 106 may include a keyway or key (not shown), while the outside surface of the detector 104 may have a corresponding keyway or key (not shown) to ensure that the detector 104 can only be inserted into the sheath 106 in a predetermined proper orientation.

In one example aspect, the sheath 106 may have a sleeve 144 that may extend along a length of the body 142. The sleeve 144 may have an open first end 148 where the light emitter 136 may be inserted, and an opposing open second end 150 for light to exit. The sleeve 144 may have a size and shape corresponding to and/or congruent with the shape of the light emitter 136, so as to receive the light emitter 136 within the sleeve 144. For example, the light emitter 136 may be inserted into a first end of the channel 144 of the sheath 106 such that the end 146 of the light emitter 136 is located at the open second end 150 of the channel. The sheath 106 may further include a lip 152 sized and shaped to correspond to the flange 133 of the handle 102. As best seen in FIG. 1, the lip 152 may abut against the flange 133 to provide a smooth transition from the handle 102 to the sheath 106.

FIG. 4 shows a side view of the probe 100 in a pivoted orientation. In the orientation shown in FIG. 4, the detector 104 has already been inserted into the sheath 106. Furthermore, the light emitter 136 has been inserted into the sleeve 144 of the sheath 106. However, as the detector/sheath combination is in the pivoted position, the detector 104 has not yet been coupled with the handle 102. Because the light emitter 136 is pivotably connected to the handle 102 via the pivot point 140, and because the light emitter is inserted into the channel 144, the combined detector/sheath/light emitter 136 is pivotable as unit about the pivot point 140. In this manner, the operator can pivot the combined detector/sheath/light emitter about the pivot point 140 until the detector 104 mates with the handle 102, resulting in the orientation shown in FIG. 1.

As discussed above, the detector includes the components needed for detecting radiation (e.g., crystals), while the handle includes the power/computer/transmitting components. The detector components are orders of magnitude more expensive than the handle components, which are relatively inexpensive. Accordingly, because the detector and handle are easily separated from each other (due to the first and second mating components), the operator may separate the detector form the handle and then dispose of the handle after each use while keeping the detector for another use. As noted above, the sheath further allows the operator to also avoid sterilizing the detector between uses. Thus, the sheath and the handle may be disposed of after each use.

While the probe 100 has been descried above as having sheath 106, in another aspect of the present invention, the sheath may be completely omitted. If the sheath is omitted, the detector 106 may have the channel for receiving the light emitter 136. In this aspect, the operator would generally need to sterilize the detector after each use, but would still be able to dispose of the handle 102.

Figure 5:
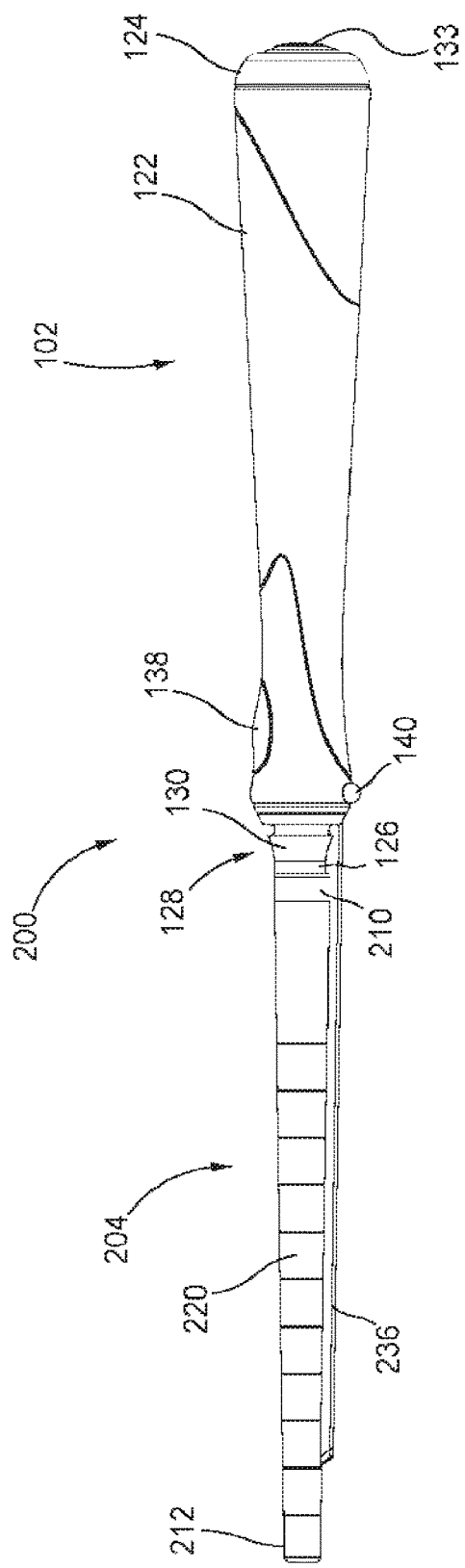
FIG. 5 is a side view of a side view of anther example probe in accordance with other aspects of the present invention.

FIG. 5 shows a side view of a probe 200 in accordance with other aspects of the present invention. The probe 200 illustrated in FIG. 5 has the handle 102 as discussed above, but has a different detector 204. The detector 204 is similar to the detector 104 and similar reference numbers are used to identify similar parts. In particular, the detector 204 may generally include an elongated body 220 having a free end 212 and an opposing end 210 for connecting to the handle 102. While not shown in FIG. 5, the detector 204 may include the same first mating component as the detector 104 for mating with the second mating component 128 of the handle 102 in the same manner as described above. Furthermore, the detector 204 may include internal components to allow for detecting radiation, similar to those of detector 104. The detector 204 is relatively longer and has a smaller diameter tip as compared to the detector 104, which makes it suitable for radiation detection of other area of the body and for different clinical applications. That is, different sized and shaped dips may be desirable depending on the particular application. As shown in FIG. 5, a longer light emitter 236 may also be used. While not shown, the same sheath concept described above with respect to detector 104 may be implemented with respect to detector 204. However, the sheath suitable for the detector 204 would be sized and shaped to fit the detector 204 (e.g., the sheath would be longer and have a smaller diameter at the tip).

Figure 6:
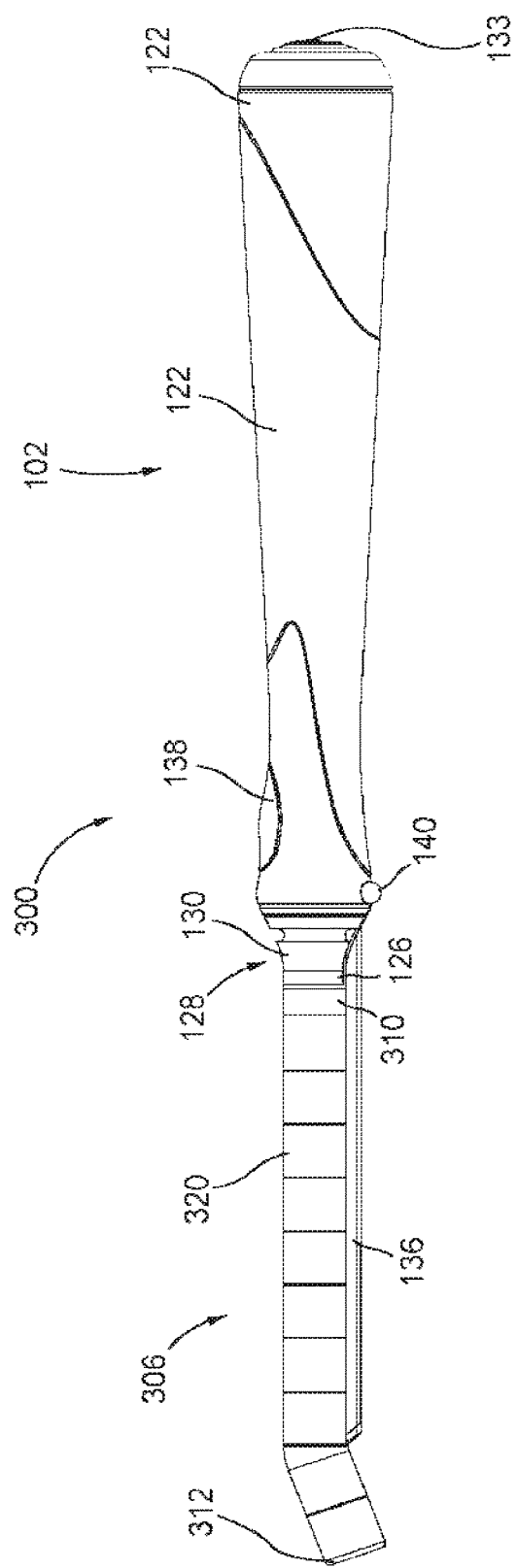
FIG. 6 is a side view of another example probe in accordance with other aspects of the present invention.

FIG. 6 shows a side view of a probe 300 in accordance with other aspects of the present invention. The probe 300 illustrated in FIG. 6 has the same handle 102 as discussed above, but has a different detector 304. The detector 304 is similar to the detector 104 and similar reference numbers are used to identify similar parts. In particular, the detector 304 may generally include an elongated body 320 having a free end 312 and an opposing end 310 for connecting to the handle 102. While not shown in FIG. 5, the detector 304 may include the same first mating component as the detector 104 for mating with the second mating component 128 of the handle 102 in the same manner as described above with respect to detector 104. Furthermore, the detector 304 may include internal components to allow for detecting radiation, similar to those of detector 104. The detector 304 has an angled tip as compared to the detector 104, which makes it suitable for radiation detection of other areas of the body and other applications. As shown in FIG. 6, the light emitter 136 may also be used. While not shown, the same sheath concept described above with respect to detector 104 may be implemented with respect to detector 304. However, the sheath suitable for the detector 304 would be sized and shaped to fit the detector 304 (e.g., would have an angled tip, among other features).

Figure 7:
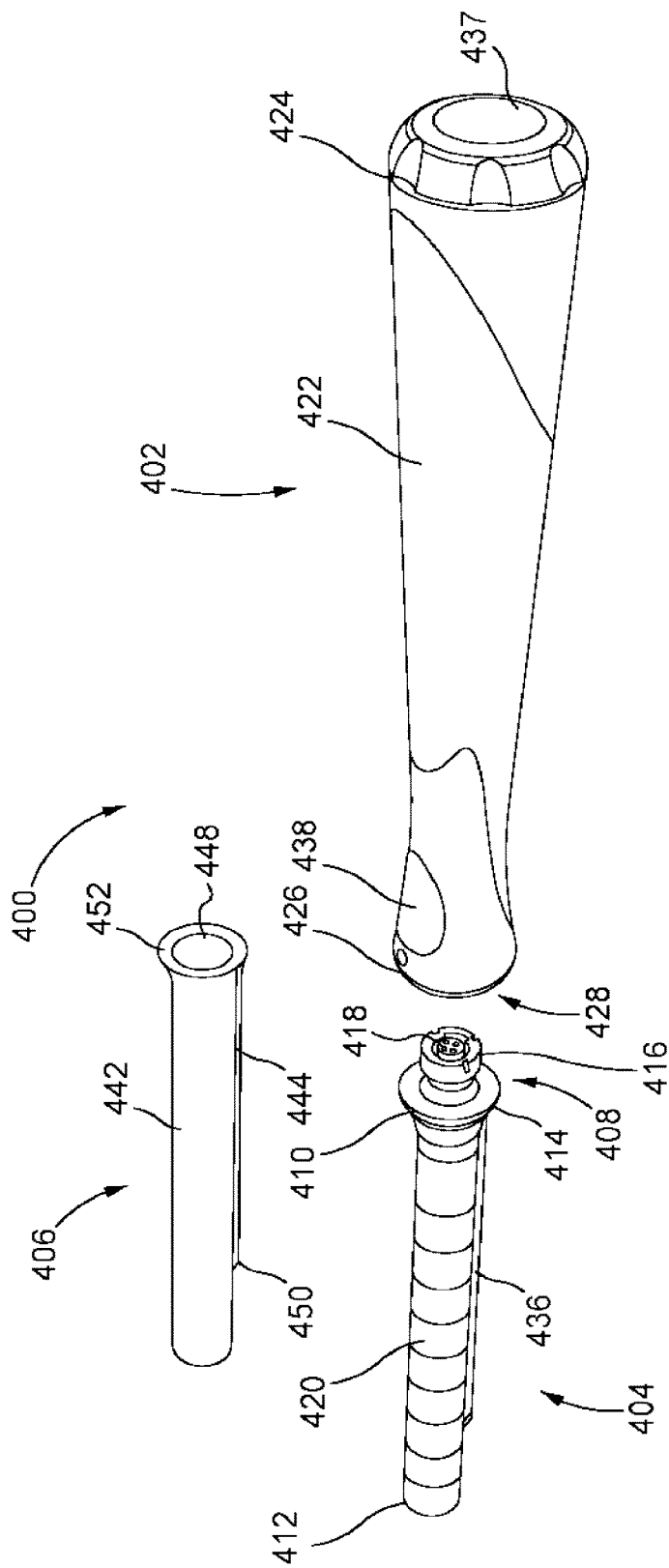
FIG. 7 is an exploded view of another example probe in accordance with other aspects of the present invention.

FIG. 7 shows an exploded view of another example probe 400 having a handle 402, a detector 404, and a sheath 406. The handle 402 is similar to the handle 102 discussed above and similar components have been given similar reference numbers. The handle 402 may generally comprise a body 422 having a free end 424 and an opposing end 426 for connecting to the detector 404. The handle 402 may generally include the electrical and computer components of the system to provide power to the detector 404 and to communicate with an instrumentation console. The handle 402 may similarly include a light button 438 and a power/wireless pairing button 437. The handle 402 may include all the same internal parts as discussed above with respect to handle 102. While the details are not viewable in FIG. 7, the handle may have a second mating component 428 that is configured to mate with the first mating component 408 of the detector 404.

The detector 404 is similar to the detector 104 and similar reference numbers are used to identify similar parts. In particular, the detector 404 may generally include an elongated body 420 having a free end 412 and an opposing end 410 for connecting to a handle. The detector 404 may include a first mating component 408 for mating with the second mating component 428 of the handle 402. As shown in FIG. 7, the first mating component 408 may have ribs 416 that mate with the second mating component 428 of the handle 402. The first mating component 408 may further include an electrical connection component 418 for mating with an electrical part of the handle 402. While the details of the second mating component 428 are not shown, the elements of the first mating component 408 would each mate with a corresponding part of the second mating component 428 of the handle 402, which would provide structural support and an electrical connection with the detector 404. As also shown in FIG. 7, the detector 404 may include a light emitter 436, which would be powered upon connection to the handle 402. The detector 404 may be coupled with the handle by pressing the first mating component 408 linearly into the second mating component 428 of the handle 402. As the light emitter 436 is not attached to the handle via a pivot point in the embodiment of FIG. 7, the detector 404 would not pivot about a pivot point. The detector 404 may further include a flange 414 for mating a sheath.

As shown in FIG. 7, the probe 400 may further include a sheath 406. The sheath 406 may generally comprise an elongated hollow body 442 that is be shaped and sized to fit around the detector 404. The sheath 406 may have a sleeve 444 that may extend along a length of the body 442. The sleeve 444 may have an open first end 448 where the light emitter 436 may be inserted, and an opposing open second end 450 for light to exit. The sheath may further include a lip 452 for resting against the flange 414 of the detector 404 once the detector 404 is inserted into the sheath 406. The sheath 406 may be pre-sterilized and be made of the same materials as discussed above with respect to sheath 106. The same type of detectors shown in FIGS. 5 and 6 (e.g., small tip and angled tip) may also be implemented as well, the only difference being that the detectors would have the first mating component shown in FIG. 7 to mate with the handle 402 instead of the first mating component that mates with handle 102.

Operation of the probes will now be described in accordance with various aspects of the present invention. Prior to the start of a radiation detecting procedure, the operator may select at least a disposable handle (e.g., one of handle 102 or handle 402) and a corresponding detector (e.g., one of detector 104, detector 204, detector 304, detector 404 or any detector that mates with the handle and is suitable for the procedure). If the operator is not using a pre-sterilized disposable sheath, then the operator may proceed to mate the handle with the detector via the first and second mating components. For the probe shown in FIGS. 1-6, the mating may be achieved by pivoting the detector about the pivot point until the first and second mating components are mated. For the probe shown in FIG. 7, mating may be achieved by inserting the detector along a central longitudinal axis of the handle until the first and second mating components are mated. Once mated, the device is ready for use. In the instance where the operator is not using a sheath, the detector would need to be sterilized following each use. If the operator wishes to avoid sterilizing the detector, then the operator may first select the sheath corresponding to the selected detector (e.g., sheath 106, sheath 406 or any other sheath that fits around the selected detector). The operator may insert the selected detector into the sheath either prior to or after mating the detector with the handle. In the embodiment of FIGS. 1-6, the light emitter may first be inserted into the channel of the sheath and then the detector may be inserted into the sheath. Notably, because the handle connects to a variety of detectors (due to the first mating component of each detector being the same and each being matable with the second mating component of the handle), the operator does not need to find a particular handle for each use, and only has to choose the correct detector.

Once mated, with or without the sheath, the operator may then operate the device to detect radiation. The operation of the device may include using the instrumentation console and system operation described in previous paragraphs and shown in the corresponding figures of U.S. Pat. App. No. 2009/0326371, "Surgical Probe Apparatus and System", which is hereby expressly incorporated by reference herein. The system may include an instrumentation console having an integral instrumentation console data link (preferably wireless), a display, a universal asynchronous receiver/transmitter (UART), a receiver, a signal processor, a power supply, and a power input. The integral instrumentation console wireless data link (hereinafter termed "console link") may be integral to, and contained by, a housing of the console. The console link may be configured for operation in conjunction with the probe link to transfer data between the probe and the instrumentation console. The console link may be implemented in any form now known or later invented utilizing, without limitation, radio frequency (RF), visible light, infra-red light, sonic and ultrasonic links and any conventional type of analog or digital modulation including, without limitation, amplitude modulation, frequency modulation, phase shift keying and frequency shift keying. Telecommunication protocols, such as the BLUETOOTH® standard as promulgated by the Bluetooth Special Interest Group, Inc. (SIG) may also be employed. A standard Serial Port Protocol (SPP) software package may also be included with the console link. Alternatively, a proprietary communication protocol may be utilized.

The UART may be a data communication interface and converter. The UART may convert data received by the console link to a serial data stream and may forward the serial data stream to receiver. Likewise, serial data generated by the receiver may be forwarded to the console link via the UART, and converted to another data format for transmission to the probe via the probe and console links. The serial data stream employed in conjunction with the UART may be configured in an Electronic Industries Alliance (EIA) serial data format, such as RS-232, RS-422 and RS-485, or may be a proprietary format. The receiver may receive the serial data stream from the UART and may convert the serial data stream to electrical display signals having predetermined voltage, current and frequency values, corresponding to the content of the data stream. Electrical display signals may be coupled to the display.

The receiver may include a digital microprocessor-based control portion configured to operate according to predetermined control logic to provide control signals for controlling the operation of the instrumentation console. Alternatively, the receiver may comprise other types of digital-based architectures utilizing, for example, a computer, microcontroller, programmable logic device and the like. The control logic of the receiver may be defined by a set of predetermined instructions, such as a computer program or "fuzzy logic." In still other aspects, the receiver may be partially or wholly comprised of analog circuitry. The receiver may incorporate, without limitation, any or all of the gamma detection features discussed in U.S. Pat. Nos. 5,732,704, 6,144,876, 6,259,095, and 6,272,373 the entire contents of each of which are hereby incorporated by reference herein in their entirety.

The signal processor may be configured to execute functions relating to analyzing, interpreting and manipulating the serial gamma data. Functions executed by signal processor may include, without limitation, filtering, smoothing, noise reduction and thresholding. For example, the signal processor may be adjusted by a user of the system to set a threshold value of the gamma data, such that data having a value below the select threshold may be ignored by the receiver and not provided to the display in the form of electrical display signals. A dynamic pitch mode may be selected wherein a baseline value may be stored and used as a threshold. Alternatively, a binary pitch mode may be selected wherein a baseline value may be stored for comparison, to determine whether a difference in detected radioactivity between a reference (such as background tissue) and a radiation source (such as target tissue) is statistically significant. The signal processor may be configured for use with analog or digital signals, or both.

The display may receive the electrical display signals and may convert the display signals into a visually perceivable indication corresponding to the data stream. The display may be any type of visual display now known or later developed including, without limitation, cathode ray tubes, fixed-format liquid crystal displays, plasma displays, active matrix liquid crystal displays and light emitting diode displays. The display may be monochromatic, color or a combination thereof, and may include a backlight.

The instrumentation console may optionally include an aural output subsystem configured to generate an aural signal corresponding to the gamma data in a predetermined manner. For example, the frequency and/or amplitude of the aural signal may be made proportional to a gamma count corresponding to the low-level electrical signal generated by the detector.

In operation, the detector of the probe may be electrically biased by bias voltage coupled thereto. Gamma radiation emitted from a source of photon emission radiation may impinge upon the detector, causing the detector to generate a low level electrical signal corresponding to predetermined characteristics of the detected gamma radiation, such as the number of photon impingements or radiation count (hereinafter generally termed "gamma data"). The preamplifier may receive and amplify low-level electrical signal generated by the detector into a corresponding output electrical signal of greater amplitude, the output electrical signal likewise corresponding to and representing the gamma data. The controller may receive the gamma data from the preamplifier via the output electrical signal. The controller converts the gamma data to a "message" having a predetermined analog and/or digital format, the message containing information relating to the gamma data in said format. The message may be periodically transmitted as a component of a probe output signal transmitted by the probe link to the console link. In one aspect of the present invention, the message may be transmitted about every fifty milliseconds. The message may contain a start transmission character, a message type character, the gamma data (two bytes), and a checksum byte (summing all other message bytes), for example. The probe output signal may also include error correction and automatic re-transmission capability to ensure the quality of the data transmission. If BLUETOOTH® technology is employed, the link may include a frequency hopping technique to avoid interference with other wireless devices.

A self-correction scheme is preferred for the probe output signal. If the probe output signal lacks such self-correction, a stronger message check such as a 16-bit cyclic redundancy check, or CRC may be used. Furthermore, if the probe output signal lacks automatic re-transmission, a bidirectional transmitter-receiver handshake scheme may be utilized wherein a console output signal issued wirelessly by the console link transmits a confirmation message to the probe link, the confirmation message being forwarded to the controller by the probe link for error-checking comparison with the message. The console link may forward the message to the UART, which may convert the message into serial format and may forward the message to the receiver. The receiver may validate the message using a checksum byte. Once the message is validated, the received gamma data may be compared against the last counter value and a difference may be calculated. Any 16-bit counter overflow may also be taken into account. If the gamma data is in the form of an absolute gamma count, a difference calculation may be desirable.

The gamma count value may be synchronized to a highly accurate internal five millisecond time interval by the receiver, each time interval being termed a "bin." This synchronization has the goal of accomplishing a stable, accurate gamma data count provided to the display in the form of electrical display signals, the electrical display signals being converted by the display to a corresponding visually perceivable image representative of the gamma data. Incoming gamma data values may be averaged by the receiver over the next ten "bins" to derive a smoothed gamma data count. The smoothing operation may be preferably configured so that it does not add or remove any gamma counts to the resulting values.

If there is loss of information (e.g., loss of messages due to wireless device being out of range, transmitter being turned off, or wireless interference malfunction), the gamma data values displayed by the display may be set to zero. If no messages are detected for a predetermined minimum period of time, such as for five seconds, the receiver may determine that the probe output signal has been lost and may provide predetermined electrical display signals to the display, such that the display visually indicates this condition to a user of the system in a predetermined manner, such as with a "NO SIGNAL" annunciation.

In some aspects, the receiver may be coupled to the signal processor. The signal processor may be configured to execute some or all of the previously noted functions relating to analyzing, interpreting and manipulating the serial gamma data. In some aspects, the aural output subsystem may be used in conjunction with, or instead of, the display. The aural output subsystem may be configured to generate an aural signal corresponding to the gamma data in a predetermined manner. For example, the frequency and/or amplitude of the aural signal may be proportional to the gamma count.

Figure 8:
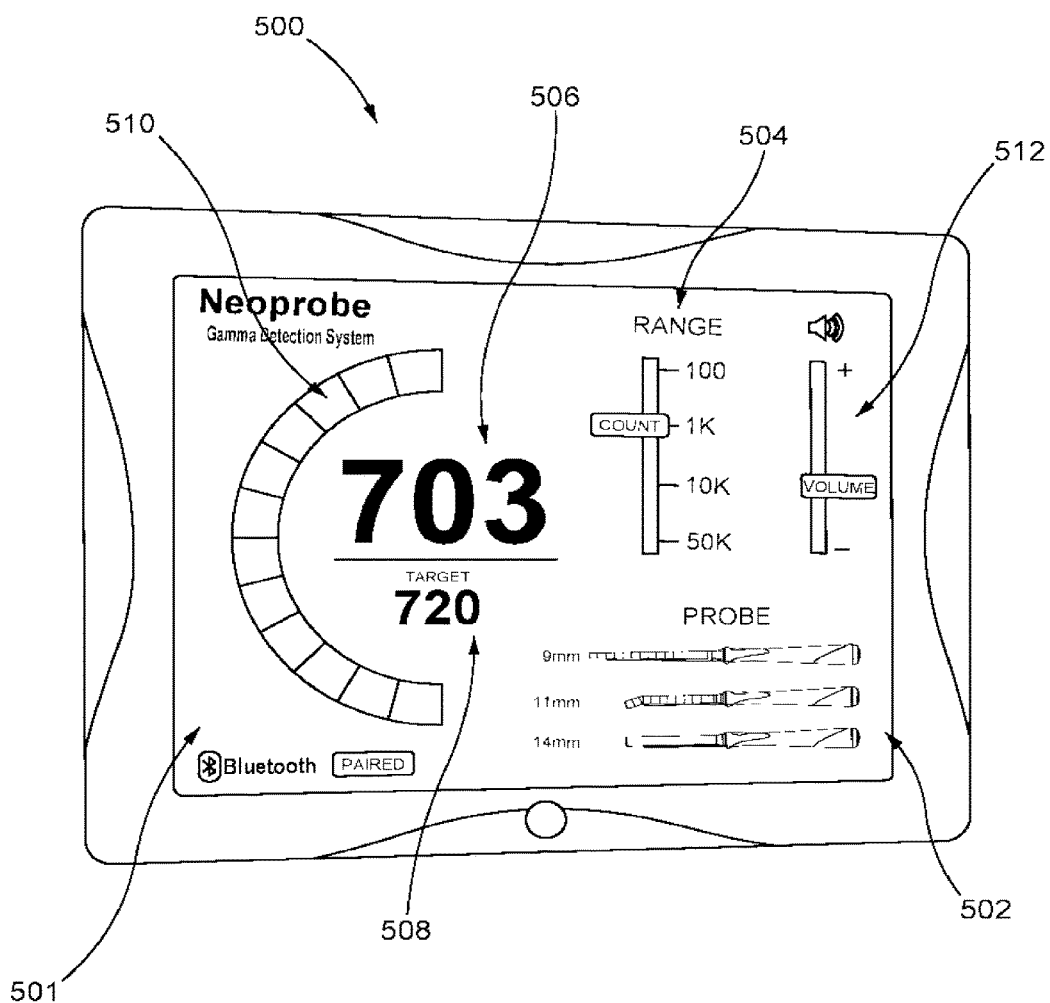
FIG. 8 shows an example instrumentation console having a graphical user interface in accordance with other aspects of the present invention.

FIG. 8 shows an example instrumentation console 500 having a graphical user interface 501 which may be used in conjunction with above-described system. The graphical user interface may be implemented on a touch screen device or any other display console/monitor which allows for operator interaction via input-output devices, such as a mouse and keyboard, for example. The graphical user interface 501 may include a probe indicator 502 which indicates to the user which type of detector is currently in communication with the system. For example, as shown in FIG. 8, the probe indicator 502 may include a visual representation of each type of detector, where the particular probe currently in communication with the system may be emphasized. In the example shown in FIG. 8, the 11 mm detector/probe is lit up, indicating that it is currently in use. The system may be configured so that part of the information being sent to the system from the probe may include an indication on which detector is being used, so that the graphical user interface can automatically indicate to the user which probe is being used. In another aspect, the system may allow the user to select which probe is being used such as by pressing the respective image on the touch screen. The probe indicator 502 may also be color coded to match a color indicator on the detector 104. The detector may have a ring have a predetermined color (e.g., one of yellow, blue, red, green, etc.) and the system may be configured such that the visual representation of that same detector on the display has the same color. The system may be programmed to have all the information necessary for each type of problem. For example, if detector type one has a yellow color ring, the operator can simply select the yellow detector image or yellow button on the display and the system will automatically select the proper settings necessary for that particular detector.

In this manner, instead of the operator needing to adjust the settings each time, a setup corresponding to the particular probe (e.g., the probe with yellow marking) can be saved for a given application. Furthermore, the system may allow for multiple probes to be in communication with the system at a given time, and the system may be configured so that when the operator picks up one of the probes in communication with the system, the image corresponding to the probe currently being held by the user may be emphasized on the graphical user interface 501.

The graphical user interface 501 may further include a selectable dynamic pitch range indicator 504, which may be selectable manually, automatically, or otherwise. The scale is set according to the usual procedure in the art based on the range in which the device will be operating. For example, if the operating area is 20,000 counts per second and the scale were set to 100, then measured readout would not work because the reading would be many times higher than the scale. Rather, the scale should be set higher so that the readings fall closer to the middle of the scale. As shown in FIG. 8, the selectable range may be displayed in terms of a bar with tick marks, each tick mark being labeled with a gamma count value associated with the tick mark. In the example shown in FIG. 8, the selectable gamma count range 504 includes four tick marks indicating 100, 1000, 10000, and 50000. In the example, the 1000 gamma count has been selected as indicated by the "count" box being located next to the 1000 tick mark.

The graphical user interface 501 may further include both a graphical and/or numerical representation of the gamma data being detected by the probe. For example, the graphical user interface 501 may include a numerical representation of the currently measured counts per second 506 above a numerical representation of the target counts per second 508, and a graphical representation 510 of the currently measured counts per second. The graphical representation 510 shows the operator how close the readings are to the top of the range. The graphical representation 510 may be in the form of a color-coded graph where the entire length of the graph corresponds to the target count (e.g., corresponds to numerical target count 508), and a portion of the graph lit up or colored corresponds to the measured count (e.g., corresponds to the numerical measure count 506). In this manner, the graphical representation 510 provides a quickly perceivable visual indication of how close the count is to the target, while the numerical representations 506, 508 provide an indication of the specific value of the measured count compared to the specific value of the target count. In another aspect, the handle 102 may include a built in display that includes the same graphical and/or numerical representation on the console 500. The display on the handle maybe an alternative to or in addition to the display on the console 500.

The graphical user interface 501 may further include a user selectable volume range 512. The user may select the volume by pressing the "plus" or "minus" symbol or by dragging the volume indicator bar. The system my implement sounds that such as frequency of beeps or other noises to indicate how high the reading. For example, slower frequency beeping or other noises may indicate lower readings and faster frequency of beeping or other noises may indicate higher readings, similar to a Geiger counter. The system may further include other audio cues, such as the start and competition of a scans. In all cases the audio may be in the form of beeps or other noises or also spoken language. In addition to or as an alternative to audio cues, the light ring 135 may be used to communicate the reading to the operator. For example, instead of or in addition to the frequency of beeps increasing with higher readings, the light ring 135 may pulse on/off at a higher frequency with higher readings and pulse on/off at a lower frequency with lower readings. In another aspect, the light ring may become brighter or dimmer instead of pulsing on/off. In yet another aspect, the light ring may be configured to change color to correspond with the reading. Thus, the light ring 135 may provide similar information regarding count readings without requiring the operator to look at the display. Furthermore, in addition to the audio and or visual feedback, haptic feedback may also be implemented in combination with or as an alternative to the other feedback. For example, the handle may include a vibrating motor similar to what is found in cell phones and other products in which tactile feedback is implemented. The motor may include an off-centered weight attached to the motor's rotational shaft that causes the motor to wobble. The amount of wobble depends by the amount of weight attached, the weight's distance from the shaft, and the speed at which the motor spins. Any suitable known tactile feedback motor system may be implemented. The motor may be configured to increase intensity of vibration with increasing count measurements. Thus, the motor can also provide similar information to the user as the display, the audio, or the light ring.

Once the operator has completed the detection procedure, the operator may then proceed to separating the components and disposing of the disposable components. The detector may be removed from handle by reversing the mating process described above. For the probes of FIGS. 1-6, the user may apply a pivoting motion of the detector away from the handle which may cause decoupling of the first mating component of the detector from the second mating component of the handle. Once decoupled, the user may then pull the light emitter out of the sheath, if the sheath is present or out of the channel of the detector, if no sheath is present. Once completely separated, the user may dispose of the handle (e.g., place the handle in a waste receptacle) as it contains parts that are disposable and/or relatively inexpensive. If a sheath is present, the operator may remove the sheath from surrounding the detector and dispose of the sheath (e.g., place the sheath in a waste receptacle). At this point, the detector may be kept for later use and may be easily reused by placing a fresh sterilized sheath around the detector and coupling the detector with a new sterile handle. If no sheath was used, the operator may sterilize the detector before it is used with a fresh handle.

Figure 9:
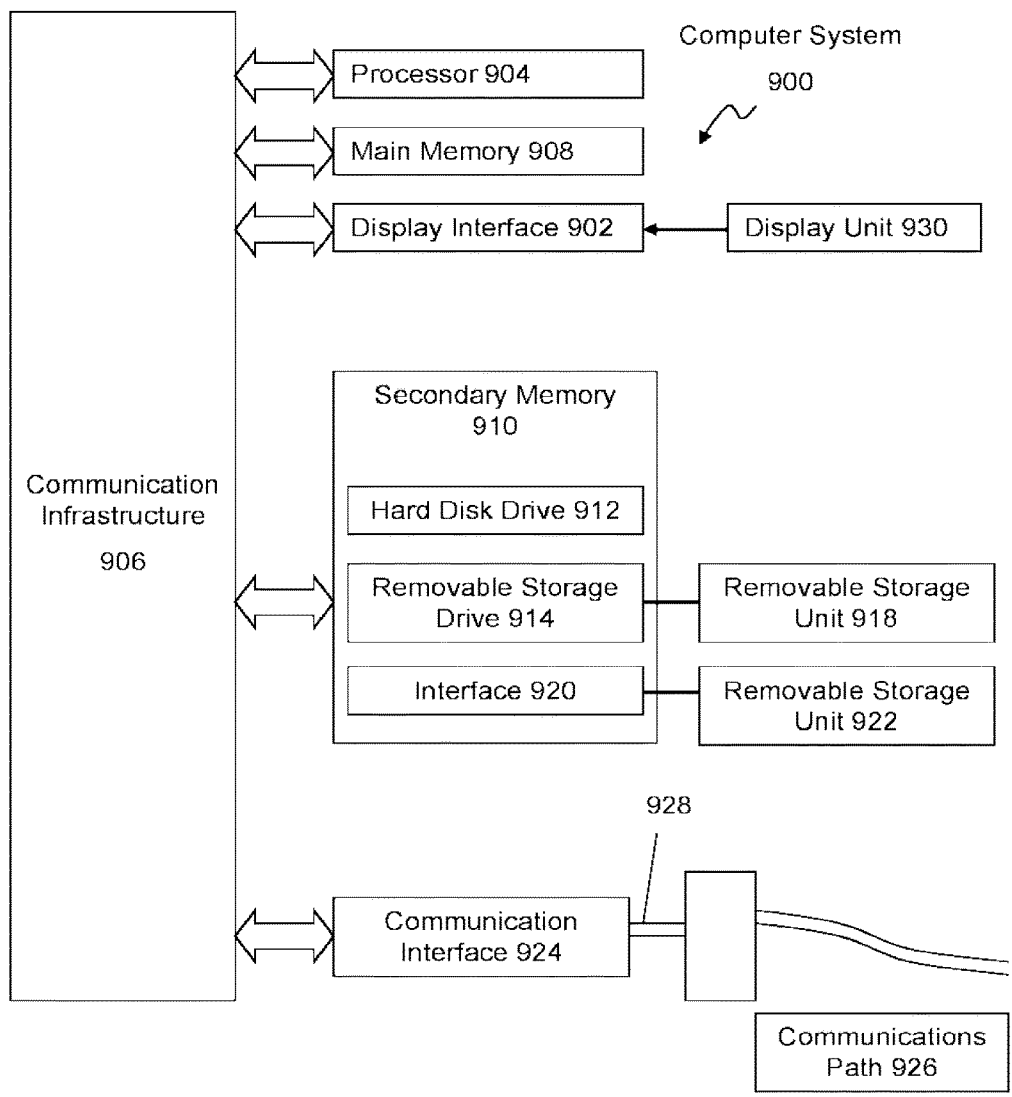
FIG. 9 shows presents an example system diagram of various hardware components and other features, for use in accordance with an aspect of the present invention.

FIG. 9 presents an exemplary system diagram of various hardware components and other features, for use in accordance with an aspect of the present invention. The present invention may be implemented using hardware, software, or a combination thereof and may be implemented in one or more computer systems or other processing systems. In one aspect, the invention is directed toward one or more computer systems capable of carrying out the functionality described herein. An example of such a computer system 900 is shown in FIG. 9.

Computer system 900 includes one or more processors, such as processor 904. The processor 904 is connected to a communication infrastructure 906 (e.g., a communications bus, cross-over bar, or network). Various software aspects are described in terms of this exemplary computer system. After reading this description, it will become apparent to a person skilled in the relevant art(s) how to implement the invention using other computer systems and/or architectures.

Computer system 900 can include a display interface 902 that forwards graphics, text, and other data from the communication infrastructure 906 (or from a frame buffer not shown) for display on a display unit 930. Computer system 900 also includes a main memory 908, preferably random access memory (RAM), and may also include a secondary memory 910. The secondary memory 910 may include, for example, a hard disk drive 912 and/or a removable storage drive 914, representing a floppy disk drive, a magnetic tape drive, an optical disk drive, etc. The removable storage drive 914 reads from and/or writes to a removable storage unit 918 in a well-known manner. Removable storage unit 918, represents a floppy disk, magnetic tape, optical disk, etc., which is read by and written to removable storage drive 914. As will be appreciated, the removable storage unit 918 includes a computer usable storage medium having stored therein computer software and/or data.

In alternative aspects, secondary memory 910 may include other similar devices for allowing computer programs or other instructions to be loaded into computer system 900. Such devices may include, for example, a removable storage unit 922 and an interface 920. Examples of such may include a program cartridge and cartridge interface (such as that found in video game devices), a removable memory chip (such as an erasable programmable read only memory (EPROM), or programmable read only memory (PROM)) and associated socket, and other removable storage units 922 and interfaces 920, which allow software and data to be transferred from the removable storage unit 922 to computer system 900.

Computer system 900 may also include a communications interface 924. Communications interface 924 allows software and data to be transferred between computer system 900 and external devices. Examples of communications interface 924 may include a modem, a network interface (such as an Ethernet card), a communications port, a Personal Computer Memory Card International Association (PCMCIA) slot and card, etc. Software and data transferred via communications interface 924 are in the form of signals 928, which may be electronic, electromagnetic, optical or other signals capable of being received by communications interface 924. These signals 928 are provided to communications interface 924 via a communications path (e.g., channel) 926. This path 926 carries signals 928 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 980, a hard disk installed in hard disk drive 970, and signals 928. These computer program products provide software to the computer system 900. The invention is directed to such computer program products.

Computer programs (also referred to as computer control logic) are stored in main memory 908 and/or secondary memory 910. Computer programs may also be received via communications interface 924. Such computer programs, when executed, enable the computer system 900 to perform the features of the present invention, as discussed herein. In particular, the computer programs, when executed, enable the processor 910 to perform the features of the present invention. Accordingly, such computer programs represent controllers of the computer system 900.

In an aspect where the invention is implemented using software, the software may be stored in a computer program product and loaded into computer system 900 using removable storage drive 914, hard drive 912, or communications interface 920. The control logic (software), when executed by the processor 904, causes the processor 904 to perform the functions of the invention as described herein. In another aspect, the invention is implemented primarily in hardware using, for example, hardware components, such as application specific integrated circuits (ASICs). Implementation of the hardware state machine so as to perform the functions described herein will be apparent to persons skilled in the relevant art(s).

In yet another aspect, the invention is implemented using a combination of both hardware and software.

Figure 10:
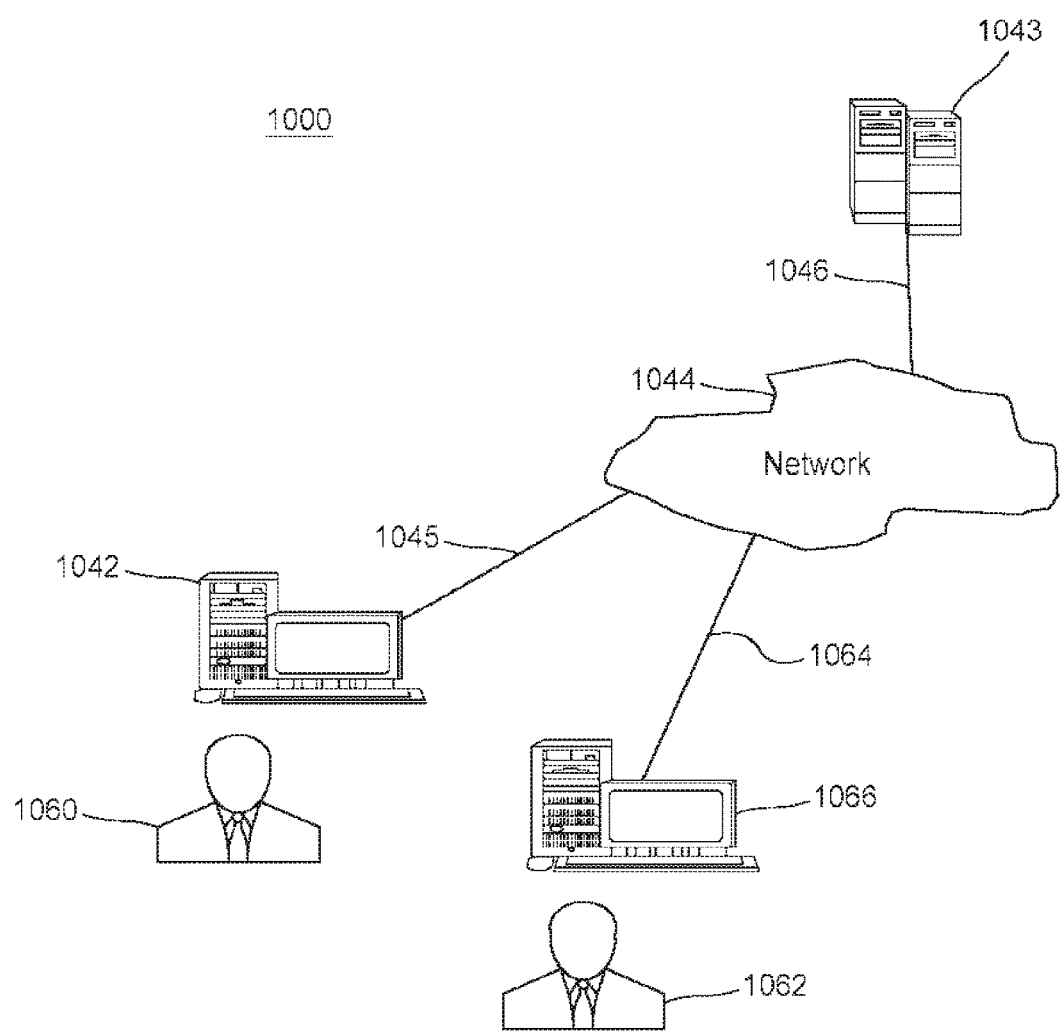
FIG. 10 is a block diagram of various example system components, in accordance with an aspect of the present invention.

FIG. 10 is a block diagram of various exemplary system components, in accordance with an aspect of the present invention. FIG. 6 shows a communication system 1000 usable in accordance with the present invention. The communication system 1000 includes one or more accessors 1060, 1062 (also referred to interchangeably herein as one or more "users") and one or more terminals 1042, 1066. In one aspect, data for use in accordance with the present invention is, for example, input and/or accessed by accessors 1060, 1062 via terminals 1042, 1066, such as personal computers (PCs), minicomputers, mainframe computers, microcomputers, telephonic devices, or wireless devices, such as personal digital assistants ("PDAs") or a hand-held wireless devices coupled to a server 1043, such as a PC, minicomputer, mainframe computer, microcomputer, or other device having a processor and a repository for data and/or connection to a repository for data, via, for example, a network 1044, such as the Internet or an intranet, and couplings 1045, 1046, 1064. The couplings 1045, 1046 and 1064 include, for example, wired, wireless, or fiberoptic links. In another aspect, the method and system of the present invention operate in a stand-alone environment, such as on a single terminal.

While example probes have been discussed above, it should be understood that other medical tools/functions may be implemented. For example the probes may include a cauterizing tip. A cauterizing tip would allow the operator to perform a cauterization while the probe is being used to locate a lymph node. That is, once the operator has found a radioactive lymph node using the probe, the operator can excise the node use the cauterizing tip. In another example aspect, the probe could include a marking device to mark the node. For example, the tip could include an ink releasing device that allows the operator to mark the radioactive node once found using the probe.

While this invention has been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects of the invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents.

The invention claimed is:
1. A hand-held probe comprising:
a detector having a first mating component and being configured to generate an electrical signal from an operative portion of the detector relating to the proximity of a source inside a patient body to the operative portion of the detector;
a handle including a second mating component configured to removably mate with the first mating component such that the handle is removably coupleable with the detector;

a sterile one-time use sheath having a closed distal end configured to removably cover the operative portion of the detector for disposal of the sheath after a medical procedure; and a display having a first numerical representation and a second numerical representation, wherein the first numerical representation is configured to depict a count generated by the detector in real-time, wherein the second numerical representation is configured to depict an operator selectable count.

2. The hand-held probe of claim 1, wherein the handle further includes:
a power source,
wherein the power source provides power to the detector when the second mating component is mated with the first mating component.

3. The hand-held probe of claim 1, further comprising:
a light emitter electrically connected to the handle, wherein the sheath includes a passageway for receiving the light emitter.

4. The hand-held probe of claim 1, wherein the detector includes:
a stacked crystal array and wherein the stacked crystal array includes:
a plurality of crystal slices;
a plurality of interconnects having electrically conductive, spaced-apart and generally parallel elements joined by electrically conductive spacers extending generally orthogonally therebetween, the spacers being rotationally offset from each other by a predetermined angle;
a plurality of electrical insulators; and
an electrically insulative housing having a plurality of slots, the crystal slices, insulators and interconnects being arranged to form an assembly wherein the crystal slices are coupled together in a parallel electrical circuit, the assembly being inserted into the housing with each of the spacers being located in corresponding slots of the housing.

5. A system, comprising:
a hand-held probe including:
a detector having a first mating component and being configured to generate a low-level electrical signal relating to a radiation source proximate the detector;
a handle including:
a second mating component configured to removably mate with the first mating component such that the handle is removably connectable with the detector;
a probe link configured to transmit a message containing gamma data relating to the low-level electrical signal; and
an instrumentation console including:
a housing;
a console link within the housing and configured to receive the message transmitted by the probe link;
a receiver electrically coupled to the console link to convert the message to corresponding electrical display signals, and a visually perceivable display electrically coupled to the receiver to convert the electrical display signals to a visually perceivable display relating to the amount of radiation detected, wherein the visually perceivable display includes a first indicator and a second indicator, wherein the first indicator relates to a current amount of radiation detected, wherein the second indicator relates to a target amount of radiation detected; and
a disposable sleeve extending distally from the first mating component of the detector corresponding to a shape of the detector and having a closed distal end, wherein the sleeve is removably coupled to the detector to provide a sterile barrier between the detector and a patient.

6. The system of claim 5, wherein the detector includes a stacked crystal array and wherein the stacked crystal array includes:
a plurality of crystal slices;
a plurality of interconnects having electrically conductive, spaced-apart and generally parallel elements joined by electrically conductive spacers extending generally orthogonally therebetween, the spacers being rotationally offset from each other by a predetermined angle;
a plurality of electrical insulators; and
an electrically insulative housing having a plurality of slots, the crystal slices, insulators and interconnects being arranged to form an assembly wherein the crystal slices are coupled together in a parallel electrical circuit, the assembly being inserted into the housing with each of the spacers being located in corresponding slots of the housing.

7. The system of claim 6, wherein the plurality of crystal slices is made from cadmium zinc tellurium.

8. The system of claim 5, wherein the detector is a scintillating device.

9. The system of claim 5, wherein the console link includes a wireless communication device configured to receive the message transmitted by the probe link.

10. A hand-held probe for locating tissue for surgical removal comprising:
a handle;
a detector attached to the handle and configured to generate a low-level electrical signal from an operative end of the detector relating to a radiation source proximate the detector;
a disposable sterile sleeve configured to removably mate with the detector and cover the operative end with a closed distal end such that the sterile sleeve is removably couplable with the detector; and
a display, wherein the display in communication with the detector, wherein the display includes a first graphical representation, a second graphical representation, and a third graphical representation, wherein the first graphical representation is configured to correspond to the low-level electrical signal generated by the detector, wherein the second graphical representation is configured to correspond to a user selectable target signal, wherein the third graphical representation is configured to graphically depict a proportional relationship between the low-level electrical signal and the target signal.

11. The hand-held probe of claim 10, wherein the sterile sleeve includes an elongated hollow body that is shaped and sized to fit around the detector.

12. The hand-held probe of claim 10, wherein the sterile sleeve includes a cylindrical body made of silicone plastic.

13. The hand-held probe of claim 10, wherein the detector includes a gamma detector for detecting gamma radiation emanating from a radiation source.

* * * * *